United States Patent [19]

Izaiku et al.

[11] Patent Number: 5,213,584
[45] Date of Patent: May 25, 1993

[54] FORMAL COMPOUNDS, FUEL OIL ADDITIVES, AND FUEL OIL COMPOSITIONS

[75] Inventors: Hiroumi Izaiku, Kanagawa; Shin-ichi Akimoto, Tokyo; Takaharu Ishizaki, Hyogo; Yoshifumi Kubo; Tohru Yasukohchi, both of Kanagawa, all of Japan

[73] Assignee: Nippon Oil and Fats Co., Ltd., Tokyo, Japan

[21] Appl. No.: 550,583

[22] Filed: Jul. 10, 1990

[30] Foreign Application Priority Data

Jul. 10, 1989 [JP] Japan .................. 1-175532

[51] Int. Cl.$^5$ .................. C10L 1/22; C07C 213/00; C07C 215/00; C07C 217/00
[52] U.S. Cl. .................. 44/433; 44/432; 44/434; 564/504; 564/505
[58] Field of Search .................. 564/504, 505; 44/432, 44/433, 434

[56] References Cited

U.S. PATENT DOCUMENTS

| | | | |
|---|---|---|---|
| 2,511,476 | 6/1950 | Loder et al. | 564/504 |
| 3,928,061 | 12/1975 | Hellsten et al. | 564/504 |
| 4,527,996 | 7/1985 | Campbell | 44/434 |

FOREIGN PATENT DOCUMENTS 20310875  4/1989  European Pat. Off. .

Primary Examiner—Jerry Johnson
Attorney, Agent, or Firm—Sughrue, Mion, Zinn, Macpeak & Seas

[57] ABSTRACT

A formal compound is represented by formula (1):

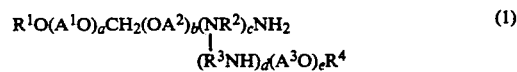

wherein $R^1$ is a hydrogen atom or a hydrocarbon group having 1 to 26 carbon atoms, $A^1$ is an alkylene group having 2 to 18 carbon atoms, a is 1 to 100, $A^2$ is an alkylene group having 2 to 4 carbon atoms, b is 1 to 5, $R^2$ is an alkylene group having 2 to 8 carbon atoms, c is 0 to 5, $R^3$ is an alkylene group having 2 to 8 carbon atoms, d is 0 to 5, $A^3$ is an alkylene group having 2 to 4 carbon atoms, e is 0 to 5, and $R^4$ is a hydrogen atom or $CH_2(OA^4)_fOR^5$, in which $A^4$ is an alkylene group having 2 to 18 carbon atoms, f is 1 to 100, and $R^5$ is hydrogen atom or a hydrocarbon group having 1 to 26 carbon atoms, and wherein each of $(A^1O)_a$, $(OA^2)_b$, $(NR^2)_c$, $(R^3NH)_d$, $(A^3O)_e$, and $(OA^4)_f$ may consist of different constituent units, a fuel oil additive comprising said formal compound and a fuel oil composition comprising a fuel oil and said formal compound.

10 Claims, 2 Drawing Sheets

FORMAL COMPOUNDS, FUEL OIL ADDITIVES, AND FUEL OIL COMPOSITIONS

FIELD OF THE INVENTION

The present invention relates to a formal compound, the use of the compound as a fuel oil additive, and a fuel oil composition containing the compound.

BACKGROUND OF THE INVENTION

Many compounds for use as deposit control additives for fuel oils such as gasoline and gas oil, have been disclosed hitherto.

Examples of such compounds include polyoxyalkylene carbamates (JP-A-53-2505 (the term "JP-A" as used herein means an "unexamined published Japanese patent application"), JP-A-55-25489, and U.S. Pat. No. 4,778,481), alkylene oxide adducts of reaction products of higher carboxylic acids with polyamines (JP-A-61-113691), polyoxyalkylenealkylamines (JP-A-62-68891), reaction products of maleic anhydride with polyamines or polyether polyamines (JP-A-62-20590), and polybutylamines (JP-A-62-241992).

Deposit control additives for fuel oils are required not only to show excellent detergent dispersiveness but also to have the properties of not forming itself into sludge and of being easily dissolved in fuel oils. It is preferable that deposit control additives be produced without use of highly toxic chemicals such as phosgene.

The conventional deposit control additives for fuel oils, however, have not fully satisfied these requirements.

SUMMARY OF THE INVENTION

As a result of intensive studies made by the present inventors, a novel compound has now been found which can be produced by easy methods without use of highly toxic chemicals and which shows excellent detergent dispersiveness and has good solubility in fuel oils.

Accordingly, an object of the present invention is to provide a formal compound which is represented by formula (1) described below and can be used as a deposit control additive for fuel oils which meets all of the above requirements.

Another object of the present invention is to provide a fuel oil additive comprising the formal compound of formula (1).

Still another object of the present invention is to provide a fuel oil composition containing the formal compound of formula (1).

DETAILED DESCRIPTION OF THE INVENTION

Figure 1:
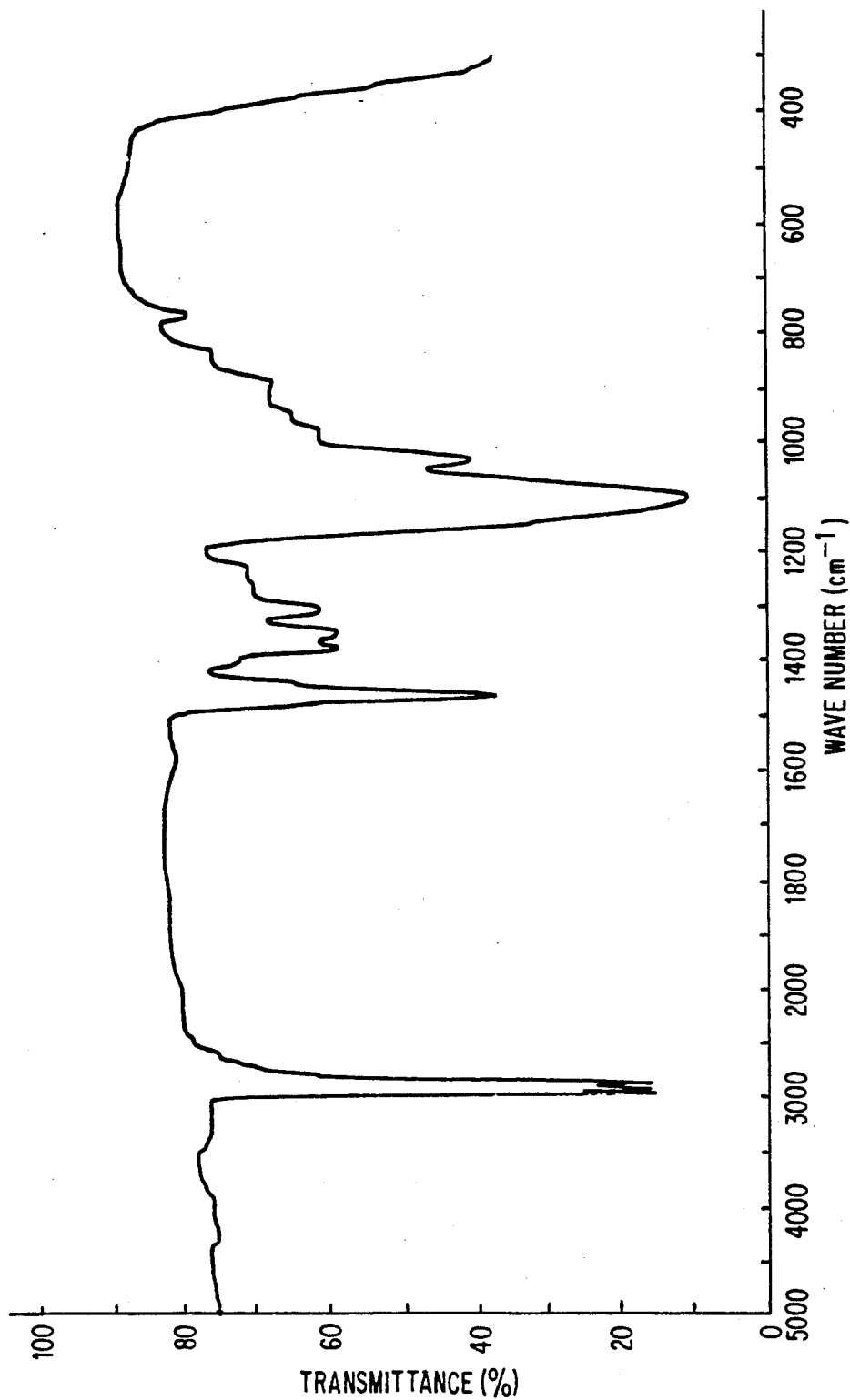
FIG. 1 is an infrared spectrum of compound B obtained in Example 1 given later.

The formal compound of the present invention is represented by the following formula (1):

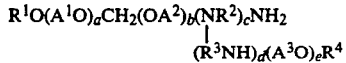

(1)

wherein $R^1$ is a hydrogen atom or a hydrocarbon group having 1 to 26 carbon atoms, $A^1$ is an alkylene group having 2 to 18 carbon atoms, a is 1 to 100, $A^2$ is an alkylene group having 2 to 4 carbon atoms, b is 1 to 5, $R^2$ is an alkylene group having 2 to 8 carbon atoms, c is 0 to 5, $R^3$ is an alkylene group having 2 to 8 carbon atoms, d is 0 to 5, $A^3$ is an alkylene group having 2 to 4 carbon atoms, e is 0 to 5, and $R^4$ is a hydrogen atom or $CH_2(OA^4)_fOR^5$, in which $A^4$ is an alkylene group having 2 to 18 Carbon atoms, f is 1 to 100, and $R^5$ is a hydrogen atom or a hydrocarbon group having 1 to 26 carbon atoms, and wherein each of $(A^1O)_a$, $(OA^2)_b$, $(NR^2)_c$, $(R^3NH)_d$, $(A^3O)_e$, and $(OA^4)_f$ may consist of different constituent units.

Examples of the hydrocarbon group having 1 to 26 carbon atoms which is represented by $R^1$ include methyl group, ethyl group, propyl group, isopropyl group, allyl group, butyl group, isobutyl group, tert-butyl group, pentyl group, isopentyl group, hexyl group, heptyl group, octyl group, 2-ethylhexyl group, nonyl group, decyl group, dodecyl group, isotridecyl group, tetradecyl group, hexadecyl group, isohexadecyl group, octadecyl group, isooctadecyl group, oleyl group, linoleyl group, octyldodecyl group, docosyl group, decyltetradecyl group, hexacosyl group, benzyl group, cresyl group, butylphenyl group, dibutylphenyl group, octylphenyl group, nonylphenyl group, dodecylphenyl group, dioctylphenyl group, dinonylphenyl group and styrenated phenyl group.

Examples of the alkylene group having 2 to 18 carbon atoms which is represented by $A^1$ include ethylene group, propylene group, butylene group, tetramethylene group, dodecylene group, tetradecylene group, hexadecylene group, octadecylene group and styrene group. Such an alkylene group is bonded to an oxygen atom to form an oxyalkylene group represented by $A^1O$.

Examples of the alkylene group having 2 to 4 carbon atoms which is represented by $A^2$ include ethylene group, propylene group, butylene group and tetramethylene group.

Examples of the alkylene groups having 2 to 8 carbon atoms respectively represented by $R^2$ or $R^3$ include ethylene group, propylene group, trimethylene group, butylene group, tetramethylene group, pentamethylene group, hexamethylene group, heptamethylene group and octamethylene group.

Examples of the alkylene group having 2 to 4 carbon atoms which is represented by $A^3$ are the same as those of the $A^2$ group.

Examples of the alkylene group having 2 to 18 carbon atoms which is represented by $A^4$ are the same as those of the $A^1$ group.

Examples of the hydrocarbon group having 1 to 26 carbon atoms which is represented by $R^5$ is the same as those of the $R^1$ group.

In the present invention, the addition amount, a, of oxyalkylene groups represented by $A^1O$ is limited to 100 or less. The reason for this is that if the amount, or number, thereof exceeds 100, such compound has an extremely high viscosity, so that removal of by-products insoluble in fuel oils becomes difficult. When the formal compound of the present is used as a fuel oil additive or in a fuel oil composition, a is preferably 5 to 70 and more preferably 10 to 50.

The formal compound of formula (1) is a formal (hereinafter referred to as a formal compound) of a polyoxyalkylene glycol or a polyoxyalkylene glycol monoalkyl ether (hereinafter referred to as an oxyalkylene compound) with a primary amine having a hydroxyalkyl group (hereinafter referred to as an alkanolamine compound).

This formalation can be carried out by reacting a mixture of an oxyalkylene compound and an alkanolamine compound with methylene chloride in the presence of an alkali.

The molar ratio of the alkanolamine compound to oxyalkylene compound used in the reaction is generally from 1:0.2 to 1:10, preferably from 1:0.3 to 1:8.

Formalation takes place also between molecules of the oxyalkylene compound or between molecules of the alkanolamine compound. From the resulting reaction product, amino group-containing compounds including the desired formal compound can be separated by passing the reaction product through an ion exchange column. If desired and necessary, purification may further be conducted by known methods such as water washing, solvent separation and column chromatograph.

The formal compound thus obtained can be used as a fuel oil additive, a lubricant additive, a dispersant, an adhesive, a plastic reformer, etc.

The formal compounds of the present invention can be made to have various properties by varying the combination of the oxyalkylene groups. A formal compound so constituted as to have a high oxyethylene content is soluble in water, while that constituted so as to contain no or few oxyethylene groups is soluble in oils. Formal compounds soluble in water are useful as dispersants for water-based system, hydrophilicityimparting agents for synthetic resins, and others.

For use as a fuel oil additive, the formal compound is required to be soluble in fuel oils and, hence, should be an oil-soluble compound. In this case, the content of oxyethylene group in the formal compound molecule is 20% by weight or less, preferably 10% by weight or less.

The formal compound of the present invention may be added, as a fuel oil additive, to a fuel oil such as gasoline and gas oil at a concentration of 5 to 10,000 ppm by weight, preferably 10 to 7,000 ppm by weight, based on the amount of the fuel oil.

The formal compound of the present invention can easily be dissolved when added to a fuel oil, if this compound is used as a solution in a solvent such as an aliphatic or aromatic hydrocarbon to provide a solution containing about 5 to 80% by weight, preferably about 20 to 60% by weight of this compound. The formal compound of the present invention, when used as a fuel oil additive or in a fuel oil composition, may be used in combination with conventional additives for fuel oils such as emulsion breaker, antioxidant, rust preventive, coloring agent, antidetonant, metal deactivator and antiicer.

The fuel oil containing the formal compound of the present invention in about 10 to 500 ppm by weight can be used to prevent the interior of engines such as engine valves from being deposited, and the fuel oil containing this compound in about 1,000 to 10,000 ppm by weight can be used to clean the deposited interior of engines.

In producing the formal compound of the present invention, the reaction product contains by-products such as those formed by formalation between molecules of an oxyalkylene compound used. However, purification of such reaction product by means of an ion exchange resin is not always necessary if the product is for use as a fuel oil additive, since these by-products do not adversely affect detergent dispersiveness.

The formal compound of the present invention, which can be obtained from an oxyalkylene compound and an alkanolamine compound, can be made to be either water-soluble or oil-soluble by suitably selecting substituent groups.

The oil-soluble formal compound, in particular, is an excellent fuel oil additive since it has excellent solubility in fuel oils and good heat resistance and shows exceeding detergent dispersiveness over a wide temperature range from low temperatures to high temperatures.

The present invention will be described more in detail by reference to the following Examples, which should not be construed as limiting the scope of the invention. In these Examples, all percents are by weight.

EXAMPLE 1

Into a 2-liter four-necked flask were introduced 619 g (0.3 mol) of polyoxybutylene glycol (hydroxyl value, 54.4; mean molecular weight, 2.063), 35.4 g (0.3 mol) of 2-hydroxyethylaminopropylamine (molecular weight, 118), and 84.2 g (1.5 mol) of potassium hydroxide. The resulting mixture was heated at 120° C. with stirring for 3 hours in a nitrogen atmosphere. Then, 45.8 g (0.54 mol) of methylene chloride (molecular weight, 84.9) was added dropwise over a period of 2 hours while the contents in the flask was kept at 120° C., and then the resulting mixture was heated at that temperature for 3 hours to allow reactions to proceed. The reaction mixture thus obtained was cooled to 50° C., 300 g of water and 500 g of n-hexane were added thereto, and then the resulting mixture was stirred for 30 minutes. The contents were then transferred to a 3-liter separation funnel and allowed to stand, an then the lower layer separated was removed. To the upper layer was added 200 g of 15% aqueous sodium chloride. This mixture was shaken sufficiently and then allowed to stand, and the resulting lower layer separated was removed. The same washing operation was repeated 5 times.

The resulting upper layer was heated at 100° to 120° C. for 2 hours at a pressure of 30 mmHg in a nitrogen atmosphere to remove the solvent, and then filtered. Thus, 585 g of a reaction product (compound A) having a hydroxyl value of 39.3, a primary amine value of 10.5, and a secondary amine value of 10.4 was obtained.

In 5 liters of a 90% aqueous solution of methanol was dissolved 40 g of the above-obtained reaction product, and the resulting solution was passed through a column packed with 10 liters of a regenerated cation exchange resin (DIAION PK-16 manufactured by Mitsubishi Kasei Corporation, Japan), thereby allowing amino group-containing compounds to be adsorbed on the cation exchange resin to separate the polyoxybutylene glycol and other compounds remaining unreacted. The amino group-containing compounds were then eluted from the column by passing 5 liters of 2% hydrochloric acid solution in methanol through the column. From the eluate, water-soluble components were removed as follows. The eluate was transferred to a 10-liter separation funnel, and 500 g of n-hexane and 4 liters of a 5% aqueous solution of potassium hydroxide were added thereto. This flask was shaken sufficiently and then allowed to stand, and the lower layer separated was removed. The upper layer was washed 5 times with 1 liter of water for each washing. The resulting upper layer was heated at 100° to 120° C. at a pressure of 30 mmHg to remove the solvent and then filtered, thereby obtaining 8.8 g of a purified product (compound B).

Elementary analysis data, chemical analysis values, and physical properties of the above-obtained compound (B) are shown below, and an infrared spectrum of the compound is given in FIG. 1.

|  | Found | Calculated |
|---|---|---|
| (1) Elementary Analysis (%) | | |
| N | 1.29 | 1.28 |
| C | 65.32 | 65.41 |
| H | 11.12 | 11.16 |
| (2) Chemical Analysis Values (KOH mg/g) | | |
| Hydroxyl value | 25.8 | 25.6 |
| Total amine value | 51.1 | 51.2 |
| Primary amine value | 25.2 | 25.6 |
| Primary amine value | 25.2 | 25.6 |
| Secondary amine value | 25.5 | 25.6 |
| Tertiary amine value | 0.4 | 0 |
| (3) Physical Properties | | |
| Kinematic viscosity (40° C.) 230 cSt | | |
| $n_D{}^{25}$ | | 1.4625 |

These analytical results indicate that the formal compound of the following formula (2) was formed by the above process.

$$HO(CHCH_2O)_{28.4}CH_2OC_2H_4NHC_3H_6NH_2 \quad (2)$$

with $C_2H_5$ branch.

EXAMPLE 2

In the same manner as in Example 1, 516 g (0.25 mol) of polyoxypropylene glycol monobutyl ether (hydroxyl value, 27.2; mean molecular weight, 2,063), 18.8 g (0.25 mol) of 3-aminopropanol, 25.5 g (0.3 mol) of methylene chloride, and 56.1 g (1 mol) of potassium hydroxide were used to carry out reactions. The resulting reaction product was washed with 15% aqueous sodium chloride and subjected to solvent removal and then filtration, in the same manner as in Example 1, thereby obtaining 412 g of a formal compound.

In 5 liters of a 90% aqueous solution of methanol were dissolved 40 g of the above-obtained formal compound. Purification of the product was effected by means of a cation exchange resin in the same manner as in Example 1, thereby obtaining 6.5 g of a purified product (compound C).

The thus-obtained compound C had the following structural formula (3).

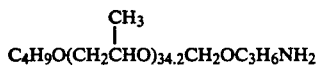

$$C_4H_9O(CH_2CHO)_{34.2}CH_2OC_3H_6NH_2 \quad (3)$$

with $CH_3$ branch.

Figure 2:
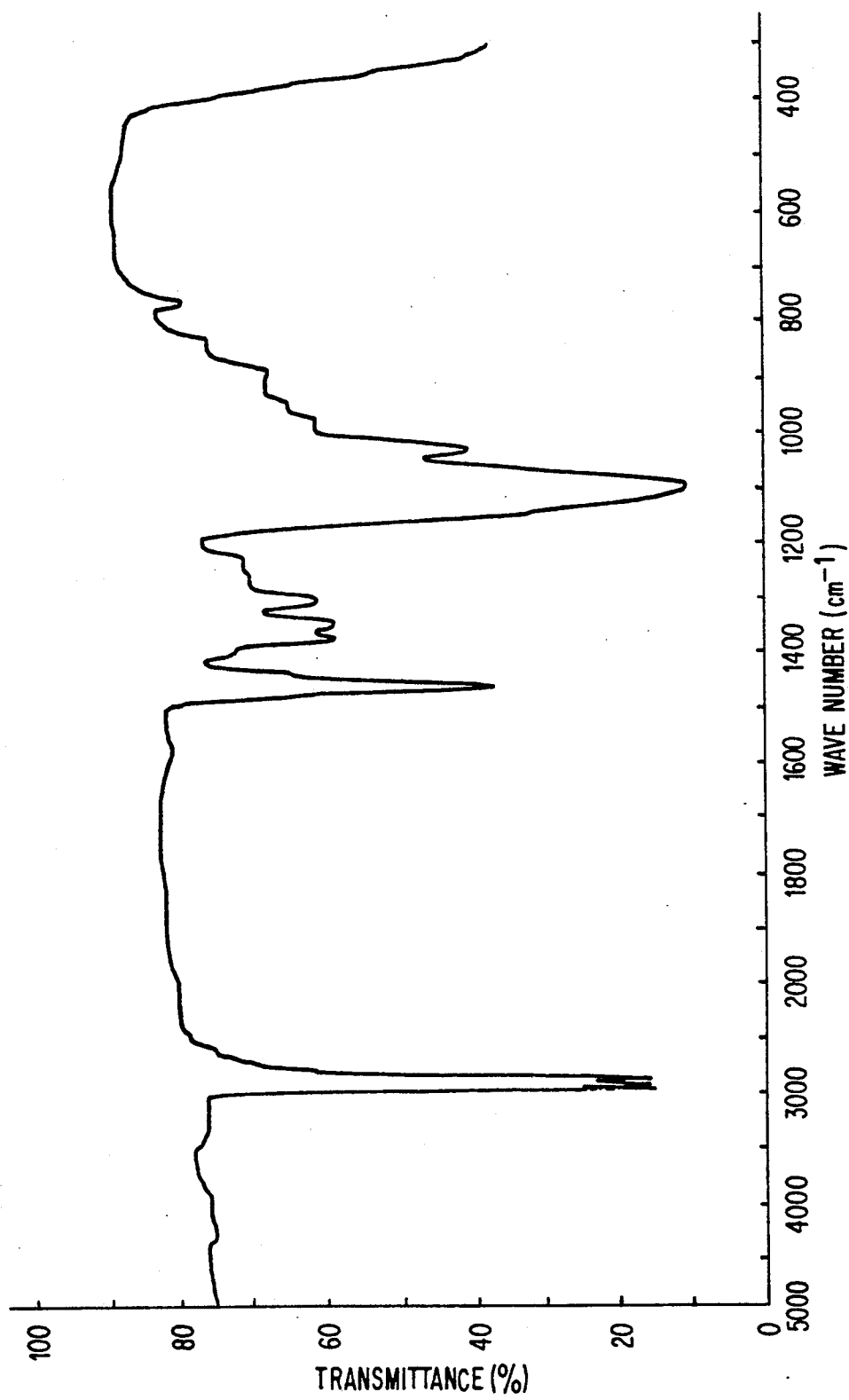
FIG. 2 is an infrared spectrum of compound C obtained in Example 2 given later.

An infrared spectrum of this compound is shown in FIG. 2, and analytical data for the compound are given below.

|  | Found | Calculated |
|---|---|---|
| (1) Elementary Analysis (%) | | |
| N | 0.65 | 0.65 |
| C | 61.85 | 61.89 |
| H | 10.53 | 10.45 |
| (2) Chemical Analysis Values (KOH mg/g) | | |

|  | Found | Calculated |
|---|---|---|
| Total amine value | 26.2 | 26.1 |
| Primary amine value | 26.0 | 26.1 |
| Secondary amine value | 0.2 | 0 |
| Tertiary amine value | 0.0 | 0 |
| (3) Physical Properties | | |
| Kinematic viscosity (40° C.) 268 cSt | | |
| $n_D{}^{25}$ | | 1.4517 |

EXAMPLE 3

In the same manner as in Example 1, 481 g (0.15 mol) of polyoxyalkylene glycol [hydroxyl value, 35.0; mean molecular weight, 3,206; a random copolymer of 10% ethylene oxide, 70% butylene oxide, and 20% C16-and-C18-mixed (60:40) α-olefin oxide (α-Olefin Oxide 168 manufactured by Oxylane Chemical Corp., Japan], 27.1 g (0.23 mol) of 2-hydroxyethylaminopropylamine, 50.5 g (0.9 mol) of potassium hydroxide, and 28.0 g (0.33 mol) of methylene chloride were used to carry out reactions.

The resulting reaction product was washed 6 times with 15% aqueous sodium chloride and subjected to solvent removal and then filtration, in the same manner as in Example 1, thereby obtaining 395 g of formal compound (compound D) represented by formula (4) and having a hydroxyl value of 31 and a primary amine value of 7.2.

$$HO(C_2H_4O)_{7.3}(CHCH_2O)_{3.1}(CHCH_2O)_{2.3}CH_2OC_2H_4NHC_3H_6NH_2 \quad (4)$$

with $C_2H_5$ and R branches.

wherein R is a mixed group of $C_{14}H_{29}$ and $C_{16}H_{33}$.

EXAMPLE 4

In the same manner as in Example 1, 530 g (0.25 mol) of polyoxypropylene glycol nonylphenyl ether (hydroxyl value, 26.5; mean molecular weight, 2,117), 63 g (0.25 mol) of the alkanolamine compound of formula (5),

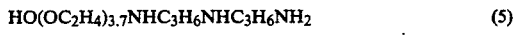

$$HO(OC_2H_4)_{3.7}NHC_3H_6NHC_3H_6NH_2 \quad (5)$$

(hydroxyl value, 223; primary amine value, 223; secondary amine value, 445; mean molecular weight, 252), 71 g (1.27 mol) of potassium hydroxide, and 42.5 g (0.5 mol) of methylene chloride were used to carry out reactions.

The resulting reaction product was washed 6 times with 15% aqueous sodium chloride and subjected to solvent removal and then filtration, in the same manner as in Example 1, thereby obtaining 465 g of formal compound (compound E) represented by formula (6) and having a hydroxyl value of 4.2, a primary amine value of 9.2, and a secondary amine value of 19.2.

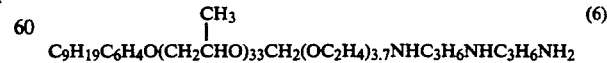

$$C_9H_{19}C_6H_4O(CH_2CHO)_{33}CH_2(OC_2H_4)_{3.7}NHC_3H_6NHC_3H_6NH_2 \quad (6)$$

with $CH_3$ branch.

EXAMPLE 5

In the same manner as in Example 1, 550 g (0.25 mol) of polyoxybutylene glycol nonylphenyl ether (hydroxyl value 25.5, mean molecular weight 2,200), 58.3 g (0.25 mol) of the alkanolamine compound of formula (7), $$\underset{\underset{C_2H_4OH}{|}}{HOC_2H_4NHC_4H_8NC_3H_6NH_2} \quad (7)$$

70 g (1.25 mol) of potassium hydroxide, and 42.5 g (0.5 mol) of methylene chloride were used to carry out reactions.

The resulting reaction product was washed 6 times with 15% aqueous sodium chloride and subjected to solvent removal and then filtration, in the same manner as in Example 1, thereby obtaining 421 g of a mixture of formal compounds represented by formulae (8) and (9). This mixture (compound F) had a hydroxyl value of 11.6, a primary amine value of 8.2, a secondary amine value of 8.3, and a tertiary amine value of 8.6.

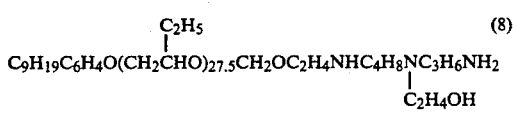

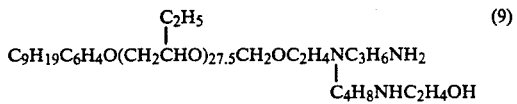

EXAMPLE 6

In the same manner as in Example 1, 550 g (0.25 mol) of the same polyoxybutylene glycol nonylphenyl ether as that used in Example 5, 28.0 g (0.12 mol) of the alkanolamine compound of formula (7),

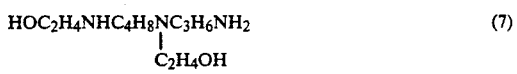

140 g (2.5 mol) of potassium hydroxide, and 50.9 g (0.6 mol) of methylene chloride were used to carry out reactions.

The resulting reaction product was washed 6 times with 15% aqueous sodium chloride and subjected to solvent removal and then filtration, in the same manner as in Example 1, thereby obtaining 502 g of formal compound (compound G) represented by formula (10) and having a hydroxy value of 2.1, a primary amine value of 7.2, and a secondary amine value of 7.6.

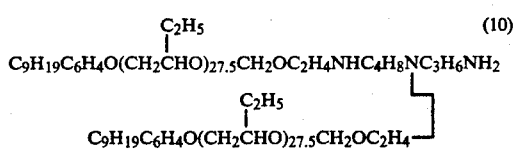

EXAMPLE 7

In the same manner as in Example 1, 525 g (0.25 mol) of a polyoxyalkylene glycol(hydroxyl value, 53.5; mean molecular weight, 2,098; a block copolymer of 60% butylene oxide and 40% tetrahydrofuran), 58 g (0.25 mol) of the alkanolamine compound of formula (11), $$HOC_2H_4(NHC_3H_6)_3NH_2 \quad (11)$$

67.3 g (1.2 mol) of potassium hydroxide, and 38.2 g (0.45 mol) of methylene chloride were used to carry out reactions.

The resulting reaction product was washed 6 times with 15% common salt solution in water and subjected to solvent removal and then filtration, in the same manner as in Example 1, thereby obtaining 480 g of formal compound (compound H) represented by formula (12) and having a hydroxyl value of 38.0, a primary amine value of 20.1, and a secondary amine value of 61.3.

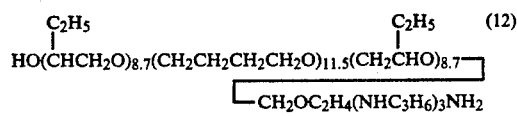

EXAMPLE 8

In the same manner as in Example 1, 425 g (0.55 mol) of a polyoxyethylene glycol isohexacosanol ether (hydroxyl value, 72.6, mean molecular weight, 773; 8.7-mol ethylene oxide adduct of FINE OXOCOL 2600 manufactured by Nissan Chemical Industries, Ltd., Japan), 103.4 g (0.55 mol) of 2-hydroxybutylaminohexylamine, 154 g (2.75 mol) of potassium hydroxide, and 74.7 g (0.88 mol) of methylene chloride were used to carry out reactions. The resulting reaction product was washed 6 times with 15% aqueous sodium chloride and subjected to solvent removal and then filtration, in the same manner as in Example 1, thereby obtaining 387 g of formal compound (compound I) represented by formula (13) and having a hydroxyl value of 4.3, a primary amine value of 23.1, and a secondary amine value of 23.3.

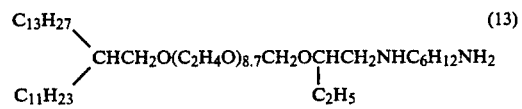

EXAMPLE 9

In the same manner as in Example 1, 537 g (0.25 mol) of a polyoxyethylene glycol methyl ether (hydroxyl value, 26.1; mean molecular weight, 2,150), 47.6 g (0.25 mol) of 2-hydroxyethyltriethylenetetramine, 56.1 g (1 mol) of potassium hydroxide, and 34 g (0.4 mol) of methylene chloride were used to carry out reactions. The resulting reaction product was washed 6 times with 15% aqueous sodium chloride and subjected to solvent removal and then filtration, in the same manner as in Example 1, thereby obtaining 461 g of formal compound (compound J) represented by formula (14) and having a hydroxyl value of 3.8, a primary amine value of 11.1, and a secondary amine value of 32.3.

$$CH_3O(C_2H_4O)_{48.1}CH_2OC_2H_4(NHC_2H_4)_3NH_2 \quad (14)$$

Physical properties of the formal compounds produced in Examples 1 to 9 are shown in Table 1 together with their oxyethylene group contents.

TABLE 1

| Formal Compound | Physical Property | | | | | | |
|---|---|---|---|---|---|---|---|
| | Kinematic Viscosity 40° C. (cSt) | Solubility (25° C.)[1] | | | Pour[2] Point (°C.) | Refractive Index ($n_D^{25}$) | Oxyethylene Group Content (%) |
| | | n-Hexane | Ethanol | Water | | | |
| Compound A | 390 | soluble | soluble | insoluble | −25 | 1.4555 | 2.0 |
| Compound B | 230 | " | " | " | −25 | 1.4625 | 2.0 |
| Compound C | 268 | " | " | " | <−25 | 1.4517 | 0 |
| Compound D | 820 | " | " | " | — | — | 11.1 |
| Compound E | 460 | " | " | " | — | — | 6.7 |
| Compound F | 510 | " | " | " | — | — | 3.6 |
| Compound G | 2200 | " | " | " | — | — | 1.9 |
| Compound H | 370 | " | " | " | — | — | 1.9 |
| Compound I | 210 | " | " | emulsifiable | — | — | 39.7 |
| Compound J | 1700 | insoluble | " | soluble | — | — | 91.9 |

Note:
[1] Solubility of 10 g of sample in 100 g of solvent.
[2] Measured in accordance with JIS K-2269.

EXAMPLE 10

Each of formal compounds A to H prepared in Examples 1 to 7 was added to gasoline, and the detergent properties of the gasoline was examined under the following conditions. The results obtained are shown in Table 2.

1) Engine used:

Type VG-20 (manufactured by Nissan Motor Co., Ltd.)

| 2) Engine-running conditions: | |
|---|---|
| (i) idling | 1 minute |
| (ii) running at 1,500 rpm with the manifold pressure of 200 mmHg | 30 minutes |
| (iii) running at 2,700 rpm with the manifold pressure of 300 mmHg | 20 minutes |
| (iv) engine stop | 9 minutes |

The engine was subjected to a continuous 200-cuycle operation, with each cycle consisting of the above (i) to (iv).

| 3) Gasoline used: JIS K 2202, #1 gasoline | |
|---|---|
| Quality | |
| density (g/cm$^3$, 15° C.) | 0.7534 |
| vapor pressure (Kgf/cm$^2$, 37.8° C.) | 0.665 |
| 10% distillate point (°C.) | 52.0 |
| 50% distillate point (°C.) | 99.5 |
| 90% distillate point (°C.) | 141.5 |
| existence gum (mg/100 ml) | 1 |

4) Evaluation method:

The formal compound is added in 120 ppm to gasoline and the engine was run on the gasoline. Before and after the running, the weights of the intake valves were measured to obtain an average deposit weight, i.e., the amount of deposits per intake valve. The results are shown in Table 2. For the purpose of comparison, gasoline containing 120 ppm of butylpoly(oxypropylene)aminoethyl carbamate and gasoline containing no such additive were tested likewise.

TABLE 2

| No. | Additive | Average Deposit Weight (g/valve) | Remarks |
|---|---|---|---|
| 1 | Compound A | 0.06 | Invention |
| 2 | Compound B | 0.04 | " |
| 3 | Compound C | 0.15 | " |
| 4 | Compound D | 0.10 | " |
| 5 | Compound E | 0.06 | " |
| 6 | Compound F | 0.05 | " |
| 7 | Compound G | 0.09 | " |
| 8 | Compound H | 0.07 | " |
| 9 | Compound A 50% Compound E 50% | 0.05 | " |
| 10 | Butylpoly (oxypropylene) aminoethyl carbamate | 0.21 | Comparative |
| 11 | No additive | 0.46 | " |

Table 2 shows that by the addition of the formal compounds according to the present invention to gasoline, the gasoline can show excellent detergent dispersiveness with little deposition on intake valves.

EXAMPLE 11

The engines with deposited intake valves resulting from the use of gasoline free of the additives in tests similar to those in Example 10 were tested using gasoline containing a relatively large amount of the formal compounds in the same manner as in Example 10 but changing 200-cycle operation to 20-cycle operation. Since gasoline usually contains an emulsion breaker, gasoline mixed with the following compound was also tested.

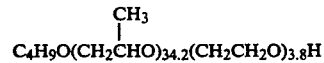

The test results are shown in Table 3. The average deposit weight before the test was 0.46 g/value. The results indicate that, when a relatively large amount of the formal compound was added to gasoline, the weight of the deposit on the intake valves decreased greatly even in 20-cycle operation demonstrating that the valves were almost completely cleaned.

TABLE 3

| No. | Additive | (ppm) | Average Deposit Weight (g/value) | Remarks |
|---|---|---|---|---|
| 1 | Compound A | 5000 | 0.04 | Invention |
| 2 | Compound B | 5000 | 0.03 | " |

TABLE 3-continued

| No. | Additive | (ppm) | Average Deposit Weight (g/value) | Remarks |
|---|---|---|---|---|
| 3 | Compound B Emulsion Breaker | 3000 2000 | 0.03 | " |
| 4 | None | 0 | 0.49 | Comparison |
| 5 | Emulsion Breaker | 2000 | 0.48 | " |

While the invention has been described in detail and with reference to specific embodiments thereof, it will be apparent to one skilled in the art that various changes and modifications can be made therein without departing from the spirit and scope thereof.

What is claimed is:

1. A formal compound represented by formula (1):

$$R^1O(A^1O)_aCH_2(OA^2)_b(NR^2)_cNH_2 \atop | \atop (R^3NH)_d(A^3O)_eR^4 \qquad (1)$$

wherein $R^1$ is a hydrogen atom or a hydrocarbon group having 1 to 26 carbon atoms, $A^1$ is an alkylene group having 2 to 18 carbon atoms, a is 1 to 100, $A^2$ is an alkylene group having 2 to 4 carbon atoms, b is 1 to 5, $R^2$ is an alkylene group having 2 to 8 carbon atoms, c is 0 to 5, $R^3$ is an alkylene group having 2 to 8 carbon atoms, d is 0 to 5, $A^3$ is an alkylene group having 2 to 4 carbon atoms, e is 0 to 5, and $R^4$ is a hydrogen atom or $CH_2(OA^4)_fOR^5$, in which $A^4$ is an alkylene group having 2 to 18 carbon atoms, f is 1 to 100, and $R^5$ is a hydrogen atom or a hydrocarbon group having 1 to 26 carbon atoms, and wherein each of $(A^1O)_a$, $(OA^2)_b$, $(NR^2)_c$, $(R^3NH)_d$, $(A^3O)_e$, and $(OA^4)_f$ may consist of different constituent units.

2. A fuel oil additive comprising a formal compound represented by formula (1):

$$R^1O(A^1O)_aCH_2(OA^2)_b(NR^2)_cNH_2 \atop | \atop (R^3NH)_d(A^3O)_eR^4 \qquad (1)$$

wherein $R^1$ is a hydrogen atom or a hydrocarbon group having 1 to 26 carbon atoms, $A^1$ is an alkylene group having 2 to 18 carbon atoms, a is 1 to 100, $A^2$ is an alkylene group having 2 to 4 carbon atoms, b is 1 to 5, $R^2$ is an alkylene group having 2 to 8 carbon atoms, c is 0 to 5, $R^3$ is an alkylene group having 2 to 8 carbon atoms, d is 0 to 5, $A^3$ is an alkylene group having 2 to 4 carbon atoms, e is 0 to 5, and $R^4$ is a hydrogen atom or $CH_2(OA^4)_fOR^5$, in which $A^4$ is an alkylene group having 2 to 18 carbon atoms, f is 1 to 100, and $R^5$ is hydrogen atom or a hydrocarbon group having 1 to 26 carbon atoms, and wherein each of $(A^1O)_a$, $(OA^2)_b$, $(NR^2)_c$, $(R^3NH)_d$, $(A^3O)_e$, and $(OA^4)_f$ may consist of different constituent units and the content of the oxyethylene group in the molecule is 20% by weight or less.

3. A fuel oil additive as claimed in claim 2, wherein a is 5 to 70.

4. A fuel oil additive as claimed in claim 2 or 3, wherein the content of oxyethylene group in the molecule is 10% by weight or less.

5. A fuel oil composition comprising a fuel oil and a formal compound represented by formula (1):

$$R^1O(A^1O)_aCH_2(OA^2)_b(NR^2)_cNH_2 \atop | \atop (R^3NH)_d(A^3O)_eR^4 \qquad (1)$$

wherein $R^1$ is a hydrogen atom or a hydrocarbon group having 1 to 26 carbon atoms, $A^1$ is an alkylene group having 2 to 18 carbon atoms, a is 1 to 100, $A^2$ is an alkylene group having 2 to 4 carbon atoms, b is 1 to 5, $R^2$ is an alkylene group having 2 to 8 carbon atoms, c is 0 to 5, $R^3$ is an alkylene group having 2 to 8 carbon atoms, d is 0 to 5, $A^3$ is an alkylene group having 2 to 4 carbon atoms, e is 0 to 5, and $R^4$ is a hydrogen atom or $CH_2(OA^4)_fOR^5$, in which $A^4$ is an alkylene group having 2 to 18 carbon atoms, f is 1 to 100, and $R^5$ is a hydrogen atom or a hydrocarbon group having 1 to 26 carbon atoms, and wherein each of $(A^1O)_a$, $(OA^2)_b$, $(NR^2)_c$, $(R^3NH)_d$, $(A^3O)_e$, and $(OA^4)_f$ may consist of different constituent units and the content of oxyethylene group in the molecule is 20% by weight or less.

6. A fuel oil composition as claimed in claim 5, wherein a is 5 to 70.

7. A fuel oil composition as claimed in claim 5 or 6, wherein the content of oxyethylene group in the molecule is 10% by weight or less.

8. A fuel oil composition as claimed in claim 5, wherein the content of the compound represented by formula (1) is from 5 to 10,000 ppm by weight based on the amount of the fuel oil.

9. A fuel oil composition as claimed in claim 6, wherein the content of the compound represented by formula (1) is from 5 to 10,000 ppm by weight based on the amount of the fuel oil.

10. A fuel oil composition as claimed in claim 7, wherein the content of the compound represented by formula (1) is from 5 to 10,000 ppm by weight based on the amount of the fuel oil.

* * * * *